US009795737B2

(12) United States Patent
Finan et al.

(10) Patent No.: US 9,795,737 B2
(45) Date of Patent: Oct. 24, 2017

(54) METHOD AND SYSTEM FOR CLOSED-LOOP CONTROL OF AN ARTIFICIAL PANCREAS

(71) Applicant: Animas Corporation, West Chester, PA (US)

(72) Inventors: Daniel Finan, Philadelphia, PA (US); Thomas McCann, Pottstown, PA (US)

(73) Assignee: ANIMAS CORPORATION, West Chester, PA (US)

( * ) Notice: Subject to any disclaimer, the term of this patent is extended or adjusted under 35 U.S.C. 154(b) by 227 days.

(21) Appl. No.: 13/834,571

(22) Filed: Mar. 15, 2013

(65) Prior Publication Data

US 2014/0276554 A1    Sep. 18, 2014

(51) Int. Cl.
*A61M 5/142*    (2006.01)
*A61M 5/172*    (2006.01)
(Continued)

(52) U.S. Cl.
CPC ....... *A61M 5/1723* (2013.01); *A61B 5/14532* (2013.01); *A61B 5/4839* (2013.01); *A61M 5/14244* (2013.01); *G06F 19/3468* (2013.01); *A61M 2005/14296* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01);
(Continued)

(58) Field of Classification Search
CPC . A61B 5/14532; A61B 5/4836; A61B 5/4839; A61M 5/1723; A61M 2205/44
USPC ..................................... 604/65–67
See application file for complete search history.

(56) References Cited

U.S. PATENT DOCUMENTS 6,088,608 A * 7/2000 Schulman .......... A61B 5/14532
                                                    600/345
7,060,059 B2    6/2006 Keith et al.
(Continued)

FOREIGN PATENT DOCUMENTS

WO       2010135670 A2    11/2010
WO    WO-2012051344 A2     4/2012
(Continued)

OTHER PUBLICATIONS

International Search Report issued in International Patent Application No. PCT/US2014/019365, dated Jun. 13, 2014, 6 pages.
(Continued)

*Primary Examiner* — Bhisma Mehta
*Assistant Examiner* — William Frehe

(57) ABSTRACT

Methods and systems for controlling an insulin pump in response to glucose measurements are responsive to a base insulin delivery profile and a temporary insulin delivery profile. These can be used, e.g., to control blood glucose level of a subject using a continuous glucose monitor and an insulin infusion pump. During a selected time range, an insulin amount for the pump to supply is determined using the temporary insulin delivery profile. Outside that time range, the insulin amount is determined using the base insulin delivery profile. The temporary insulin delivery profile can specify an exact amount to be supplied (a "hard" profile), a nominal amount to be supplied if doing so does not drive glucose out of a desired zone ("soft"), or a soft profile with a minimum amount of insulin to be delivered ("semi-soft").

12 Claims, 8 Drawing Sheets

(51) Int. Cl.
*A61B 5/145* (2006.01)
*A61B 5/00* (2006.01)
*G06F 19/00* (2011.01)

(52) U.S. Cl.
CPC ... *A61M 2205/502* (2013.01); *A61M 2205/52* (2013.01); *A61M 2209/01* (2013.01); *A61M 2230/201* (2013.01); *G06F 19/3437* (2013.01)

(56) References Cited

U.S. PATENT DOCUMENTS

| | | | |
|---|---|---|---|
| 7,276,029 | B2 | 10/2007 | Goode, Jr. et al. |
| 8,062,249 | B2 | 11/2011 | Wilinska et al. |
| 2008/0183060 | A1* | 7/2008 | Steil .................. A61B 5/14532 600/365 |
| 2010/0292634 | A1 | 11/2010 | Kircher, Jr. et al. |
| 2010/0295686 | A1 | 11/2010 | Sloan et al. |
| 2011/0208156 | A1 | 8/2011 | Doyle, III et al. |
| 2011/0257627 | A1 | 10/2011 | Hovorka |
| 2011/0313680 | A1 | 12/2011 | Doyle, III et al. |

FOREIGN PATENT DOCUMENTS

| | | | | |
|---|---|---|---|---|
| WO | 2012058694 | A2 | 5/2012 | |
| WO | WO 2012058694 | A2 * | 5/2012 | ........ A61M 5/14244 |

OTHER PUBLICATIONS

Written Opinion issued in International Patent Application No. PCT/US2014/019365, dated Jun. 13, 2014, 7 pages.

Grosman, Benyamin, Ph.D. et al. "Zone Model Predictive Control: A Strategy to Minimize Hyper and Hypoglycemic Events" Journal of Diabetes Science and Technology, vol. 4, Issue 4, Jul. 2010 (15 pgs.).

Gillis, Rachel et al., "Glucose Estimation and Prediction through Meal Responses Using Ambulatory Subject Data for Advisory Mode Model Predictive Control", Journal of Diabetes Science and Technology, vol. 1, Issue 6, Nov. 2007 (9 pgs.).

Wang, Youqing et al., "Closed-Loop Control of Artificial Pancreatic β-Cell in Type 1 Diabetes Mellitus Using Model Predictive Iterative Learning Control" IEEE Transactions on Biomedical Engineering, vol. 57, No. 2, Feb. 2010 (9 pgs.).

Soru, Paola et al.., "MPC Based Artificial Pancreas; Strategies for Individualization and Meal Compensation" Annual Reviews in Control 36, p. 118-128 (2012) (11 pgs.).

Cobelli et al., "Artificial Pancreas: Past, Present, Future", Perspectives in Diabetes, vol. 60, Nov. 2011 (11 pgs.).

Magni et al., "Run-to-Run Tuning of Model Predictive Control for Type 1 Diabetes Subjects: In Silico Trial" Journal of Diabetes Science and Technology, vol. 3, Issue 5, Sep. 2009 (8 pgs.).

Lee et al., "A Closed-Loop Artificial Pancreas Using Model Predictive Control and a Sliding Meal Size Estimator" Journal of Diabetes Science and Technology, vol. 3, Issue 5, Sep. 2009 (9 pgs.).

Lee et al., "A Closed-Loop Artificial Pancreas based on MPC: Human Friendly Identification and Automatic Meal Disturbance Rejection" Proceedings of the 17th World Congress, the International Federation of Automatic Control, Seoul Korea Jul. 6-11, 2008; (6 pgs.).

Magni et al., "Model Predictive Control of Type 1 Diabetes: An in Silico Trial" Journal of Diabetes Science and Technology, vol. 1, Issue 6, Nov. 2007 (9 pgs.).

Wang et al., "Automatic Bolus and Adaptive Basal Algorithm for the Artificial Pancreatic βCell" Diabetes Technology and Therapeutics, vol. 12, No. 11, 2010 (10 pgs.).

Programming Your Pump found at http://dtc.ucsf.edu/types-of-diabetes/type2/treatment-of-type-2-diabetes/medications-and-therapies/type-2-pump-rx/how-to-use-your-pump/pr . . . as printed on Feb. 13, 2013 @ 8:11 AM (12 pgs.).

Advanced Programming found at http://dtc.ucsf.edu/types-of-diabetes/type2/treatment-of-type-2-diabetes/medications-and-therapies/type-2-pump-rx/how-to-use-your-pump/pr . . . as printed on Feb. 13, 2013 @ 8:10 AM (9 pgs.).

Temporary Basal found at http://dtc.ucsf.edu/types-of-diabetes/type2/treatment-of-type-2-diabetes/medications-and-therapies/type-2-pump-rx/how-to-use-your-pump/pr . . . as printed on Feb. 13, 2013 @ 8:09 AM (10 pgs.).

Percival, Matthew W. et al., "Closed-Loop Conrol of an Artificial Pancreatic Beta Cell Using Multi-Parametric Model Predictive Conrol," Department of Chemical Engineering, University of California, Santa Barbara, Sansum Diabetes Research Institute, originally presented Nov. 17, 2008, 11 pages.

* cited by examiner

METHOD AND SYSTEM FOR CLOSED-LOOP CONTROL OF AN ARTIFICIAL PANCREAS

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and/or hypoinsulinemia has been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External biologic agents such as insulin have commonly been administered as multiple daily injections of a mixture of rapid- and intermediate-acting drugs via a hypodermic syringe. It has been found that the degree of glycemic control achievable in this way is suboptimal because the delivery is unlike physiological hormone production, according to which hormone enters the bloodstream at a lower rate and over a more extended period of time. Improved glycemic control may be achieved by the so-called intensive hormone therapy which is based on multiple daily injections, including one or two injections per day of a long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections.

Substantial improvements in diabetes therapy have been achieved by the development of drug delivery devices that relieve the patient of the need for syringes or drug pens and the need to administer multiple daily injections. The drug delivery device allows for the delivery of a drug in a manner that bears greater similarity to the naturally occurring physiological processes and can be controlled to follow standard or individually-modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body, and are generally controlled via a user interface built in to the device or arranged on a separate remote device.

Blood or interstitial glucose monitoring is required to achieve acceptable glycemic control. For example, delivery of suitable amounts of insulin by the drug delivery device requires that the patient frequently determine his or her blood glucose level and manually input this value into a user interface for the external pumps. The user interface or a corresponding controller then calculates a suitable modification to the default or currently in-use insulin delivery protocol, i.e., dosage and timing, and subsequently communicates with the drug delivery device to adjust its operation accordingly. The determination of blood glucose concentration is typically performed by means of an episodic measuring device such as a hand-held electronic meter which receives blood samples via enzyme-based test strips and calculates the blood glucose value based on the enzymatic reaction. Throughout this disclosure, the terms "patient," "subject," and "user" (i.e., user of a drug delivery device) are used interchangeably.

Continuous glucose monitoring (CGM) has also been utilized over the last twenty years with drug delivery devices to allow for closed loop control of the insulin(s) being infused into the diabetic patients. To allow for closed-loop control of the infused insulins, proportional-integral-derivative ("PID") controllers have been utilized with mathematical model of the metabolic interactions between glucose and insulin in a person. The PID controllers can be tuned based on simple rules of the metabolic models. However, when the PID controllers are tuned or configured to aggressively regulate the blood glucose levels of a user, overshooting of the set level can occur, which is often followed by oscillations, which is highly undesirable in the context of regulation of blood glucose. Model predictive controllers ("MPC") have also been used. The MPC controller has been demonstrated to be more robust than PID because MPC considers the near future effects of control changes and constraints in determining the output of the MPC, whereas PID typically involves only past outputs in determining future changes. MPC therefore is more effective than PID in view of the complex interplay between insulin, glucagon, and blood glucose. Constraints can be implemented in the MPC controller such that MPC prevents the system from running away when a control limit has been reached. For example, some schemes do not deliver any glucose during a hypoglycemic excursion. Another benefit of MPC controllers is that the model in the MPC can, in some cases, theoretically compensate for dynamic system changes whereas a feedback control, such as PID control, such dynamic compensation would not be possible.

Additional details of the MPC controllers, variations on the MPC and mathematical models representing the complex interaction of glucose and insulin are shown and described in the following documents:
U.S. Pat. No. 7,060,059;
US Patent Application Nos. 2011/0313680 and 2011/0257627,
International Publication WO 2012/051344,
Percival et al., "Closed-Loop Control and Advisory Mode Evaluation of an Artificial Pancreatic β Cell: Use of Proportional-Integral-Derivative Equivalent Model-Based Controllers" Journal of Diabetes Science and Technology, Vol. 2, Issue 4, July 2008.
Paola Soru et al., "MPC Based Artificial Pancreas; Strategies for Individualization and Meal Compensation" Annual Reviews in Control 36, p. 118-128 (2012),
Cobelli et al., "*Artificial Pancreas: Past, Present, Future*" Diabetes Vol. 60, November 2011;
Magni et al., "*Run-to-Run Tuning of Model Predictive Control for Type* 1 *Diabetes Subjects: In Silico Trial*" Journal of Diabetes Science and Technology, Vol. 3, Issue 5, September 2009.

Lee et al., "A Closed-Loop Artificial Pancreas Using Model Predictive Control and a Sliding Meal Size Estimator" Journal of Diabetes Science and Technology, Vol. 3, Issue 5, September 2009;

Lee et al., "*A Closed-Loop Artificial Pancreas based on MPC: Human Friendly Identification and Automatic Meal Disturbance Rejection*" Proceedings of the 17$^{th}$ World Congress, The International Federation of Automatic Control, Seoul Korea Jul. 6-11, 2008;

Magni et al., "*Model Predictive Control of Type* 1 *Diabetes: An in Silico Trial*" Journal of Diabetes Science and Technology, Vol. 1, Issue 6, November 2007;

Wang et al., "Automatic Bolus and Adaptive Basal Algorithm for the Artificial Pancreatic β-Cell" Diabetes Technology and Therapeutics, Vol. 12, No. 11, 2010; and Percival et al., "Closed-Loop Control of an Artificial Pancreatic β-Cell Using Multi-Parametric Model Predictive Control" Diabetes Research 2008.

All articles or documents cited in this application are hereby incorporated by reference into this application as if fully set forth herein.

Drug delivery devices generally provide insulin at a "basal rate," i.e., provide a certain amount of insulin every few minutes in a pre-programmed, daily pattern. Some drug delivery devices also permit the user to specify a "temporary basal," in which the normal daily cycle is altered for a selected length of time.

Some drug delivery devices permit the user to manually request that a "bolus," a specified amount of insulin, be delivered at a specified time. For example, before a meal, the user can request a bolus of additional insulin be delivered to process the glucose produced by digestion of the meal. Some drug delivery devices permit the specified amount to be delivered over a period of time rather than all at once; time-extended delivery is referred to as an "extended bolus."

SUMMARY OF THE DISCLOSURE

However, in prior schemes, temporary basals and extended boluses are manually-requested and manually-controlled. In order to obtain the desired benefit from these schemes, users are required to: (a) measure their blood glucose, (b) know the effect of insulin on blood glucose ("insulin sensitivity factor" or "ISF"), (c) know how many grams of carbohydrates they are eating, (d) know how much insulin is required for a given amount of carbohydrate ("insulin-to-carbohydrate ratio"), (e) know the effects of exercise and other activities on their blood glucose, and (f) program the pump correspondingly. These five factors are merely one example that users of insulin therapy have to contend with. Inaccurate information in any of these categories can lead to glucose excursions if, e.g., the user specifies too large or too small a bolus for a given meal.

Moreover, glucose measurements in the body show significant variability due to frequent changes in the glucose level and variability in the measurement instruments. Control techniques tuned to appropriately respond to this variability may not be able to respond correctly in the presence of glucose transients (high or low) resulting from temporary basals or extended boluses. Accordingly, there is a continuing need for a way of delivering an appropriate amount of insulin based on continuous glucose measurements, and of providing temporary-basal and extended-bolus functionality that does not negatively affect the controller while maintaining safeguards on blood glucose level.

In one aspect, therefore, applicants have devised a method to control an infusion pump responsive to a controller that receives data from a glucose sensor. The method can be achieved by measuring a glucose level of a physiological fluid from a user with the glucose sensor and automatically performing the following steps using the controller:

receiving from the glucose sensor respective glucose level measurements for each time interval of a series of discrete time intervals;

receiving a temporary insulin delivery profile extending over a selected time range of the time intervals;

calculating a candidate insulin delivery amount for a selected one of the time intervals based on a model predictive controller that:

predicts an excursion of the glucose level from a selected target glucose range using at least some of the glucose measurements;

computes an estimated insulin delivery amount; and adjusts the estimated insulin delivery amount to provide the candidate insulin delivery amount, the adjustment performed in accordance with the predicted excursion, the base insulin delivery profile, or, if the selected time interval is in the selected range, the temporary insulin delivery profile;

determining an approved insulin delivery amount from the candidate insulin delivery amount; and commanding the infusion pump to deliver the approved insulin delivery amount.

In another aspect, applicants have also devised a method to control an infusion pump responsive to a controller that receives data from a glucose sensor. The method can be achieved by measuring a glucose level of physiological fluid from a user with the glucose sensor and performing the following steps using the controller:

receiving from the glucose sensor respective glucose level measurements for each time interval of a series of discrete time intervals;

receiving a temporary insulin delivery profile extending over a selected time range of the time intervals;

calculating a candidate insulin delivery amount for a selected one of the time intervals based on a model predictive controller that:

if the selected time interval is outside the selected range, predicts an excursion of the glucose level from a selected target glucose range using at least some of the glucose measurements;

computes an estimated insulin delivery amount; and adjusts the estimated insulin delivery amount to provide the candidate insulin delivery amount, the adjustment performed in accordance with the predicted excursion and the base insulin delivery profile; and if the selected time interval is in the selected range, retrieves the candidate insulin delivery amount for the selected time interval from the temporary insulin delivery profile;

determining an approved insulin delivery amount from the candidate insulin delivery amount; and commanding the infusion pump to deliver the approved insulin delivery amount.

In yet a further aspect, applicants have also devised an apparatus for the delivery of insulin. The apparatus may include the following components:

a) a glucose monitor adapted to measure respective glucose levels of a subject at discrete time intervals and provide respective glucose measurement data indicating each measured glucose level;

b) an insulin infusion pump configured to deliver insulin in response to a delivery control signal;
c) a memory configured to store a base insulin delivery profile;
d) an interface adapted to selectively receive a temporary insulin delivery profile extending over a selected time range of the time intervals and to provide a first signal indicating whether the temporary insulin delivery profile was received; and
e) a controller adapted to, for each of a plurality of the discrete time intervals:
   i) receive the glucose measurement data for that time interval from the glucose monitor;
   ii) determine an insulin delivery amount for that time interval using model predictive control based on a selected target glucose concentration range, the received glucose measurement data, the stored base insulin delivery profile, or, in response to the first signal and if that time interval is in the selected time range, the received temporary insulin delivery profile; and
   iii) provide to the insulin infusion pump a delivery control signal corresponding to the determined insulin delivery amount, whereby a corresponding amount of insulin is delivered.

In another aspect, there is provided apparatus for the delivery of insulin, the apparatus. The apparatus may include the following components:
a) a glucose monitor adapted to measure respective glucose levels of a subject at discrete time intervals and provide respective glucose measurement data indicating each measured glucose level;
b) an insulin infusion pump configured to deliver insulin in response to a delivery control signal;
c) a memory configured to store a base insulin delivery profile;
d) an interface adapted to receive a temporary insulin delivery profile extending over a selected time range of the time intervals; and
e) a controller adapted to, for each of a plurality of the discrete time intervals:
   i) receive the glucose measurement data for that time interval from the glucose monitor;
   ii) if that time interval is in the selected time range, retrieve a corresponding insulin delivery amount from the temporary insulin delivery profile, or else determine an insulin delivery amount for that time interval using model predictive control based on a selected target glucose concentration range, the received glucose measurement data, and the base insulin delivery profile; and
   iii) provide to the insulin infusion pump a delivery control signal corresponding to the insulin delivery amount, whereby a corresponding amount of insulin is delivered.

These aspects provide increased user control over insulin level by permitting temporary basals and extended boluses to be specified without requiring complex insulin- and glucose-level calculations. In various aspects, temporary basals and extended boluses are handled by a model predictive controller just as standard basals are, reducing the likelihood of model-induced insulin transients.

Accordingly, in any of the aspects described earlier, the following features may also be utilized in various combinations with the previously disclosed aspects. For example, the step of receiving a temporary insulin delivery profile may include receiving a profile modifier and applying the profile modifier to the base insulin delivery profile to produce the temporary insulin delivery profile; the adjustment may include: if the selected time interval is in the selected range, adjusting the estimated delivery amount in accordance with the predicted excursion and the temporary insulin delivery profile; and if the selected time interval is not in the selected range, adjusting the estimated delivery amount in accordance with the predicted excursion and the base insulin delivery profile; alternatively, the adjustment may include: if the selected time interval is in the selected range, adjusting the estimated delivery amount in accordance with the predicted excursion and the temporary insulin delivery profile and constraining the calculated insulin delivery amount to be at least a difference between the temporary insulin delivery profile and the base insulin delivery profile in the selected time interval; and if the selected time interval is not in the selected range, adjusting the estimated delivery amount in accordance with the predicted excursion and the base insulin delivery profile; the determining-approved-amount step may include providing the candidate insulin delivery amount as the approved insulin delivery amount; alternatively, the determining-approved-amount step may include reducing the candidate delivery amount to provide the approved insulin delivery amount according to a safety model; the temporary insulin delivery profile may include former and latter subranges of the selected time range and specifies higher amounts or rates of insulin delivery in the former subrange than in the latter subrange; the determining-approved-amount step may include using a safety model to determine whether a hypoglycemic excursion is predicted and, if so, reducing the candidate delivery amount to provide the approved insulin delivery amount. Furthermore, the interface can be adapted to receive the temporary insulin delivery profile by receiving change information and modifying the stored base insulin delivery profile in the selected time range according to the change information to provide the temporary insulin delivery profile; the controller may be adapted to determine the insulin delivery amount for a selected time interval using: (a) if the temporary insulin delivery profile was not received or the selected time interval is outside the selected time range, the selected target glucose concentration range, the received glucose measurement data, the stored base insulin delivery profile; (b) otherwise, the selected target glucose concentration range, the received glucose measurement data, and the received temporary insulin delivery profile; the controller can further be adapted to, in response to the first signal and if a selected time interval is in the selected time range, constrain the determined insulin delivery amount for the selected time interval to be at least a difference between respective values of the temporary insulin delivery profile and the stored base insulin delivery profile for the selected time interval; the controller can further be adapted to: a) predict an excursion of a glucose level of the subject from the selected target glucose range using a safety model and at least some of the glucose measurement data for a plurality of the time intervals; and b) reduce the determined insulin delivery amount according to the predicted excursion; the temporary insulin delivery profile may include former and latter subranges of the selected time range and specifies higher amounts or rates of insulin delivery in the former subrange than in the latter subrange; the glucose monitor may include a plurality of glucose sensors; the interface can further be adapted to provide an activation signal and the controller, in response to the activation signal, retrieves the stored base insulin delivery profile and retrieves or determines the insulin delivery amount; the controller can further be adapted to: a)

predict an excursion of a glucose level of the subject from the selected target glucose range using a safety model and at least some of the glucose measurement data for a plurality of the time intervals; and b) reduce the determined insulin delivery amount according to the predicted excursion; the glucose monitor may include a plurality of glucose sensors; and the interface can further be adapted to provide an activation signal and the controller, in response to the received activation signal, to retrieve the stored base insulin delivery profile and retrieve or determine the insulin delivery amount.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormone, biologically active materials, pharmaceuticals or other chemicals that cause a biological response (e.g., glycemic response) in the body of a user or patient.

Figure 1:
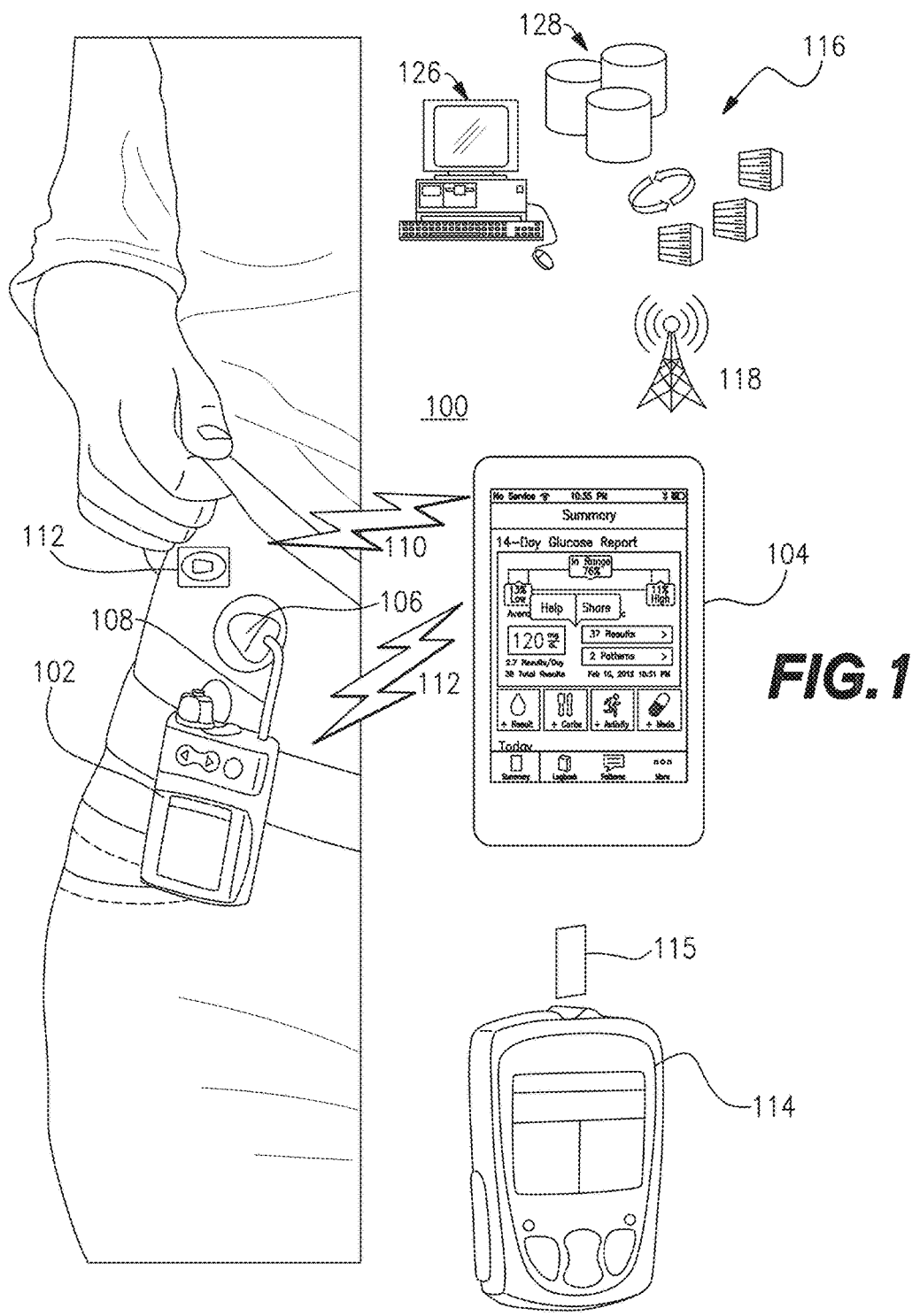
FIG. 1 illustrates the system in which a controller for the pump or glucose monitor(s) is separate from both the infusion pump and the glucose monitor(s) and in which a network can be coupled to the controller to provide near real-time monitoring.

FIG. 1 illustrates a drug delivery system 100 according to an exemplary embodiment that utilizes the principles of the invention. Drug delivery system 100 includes a drug delivery device 102 and a remote controller 104. Drug delivery device 102 is connected to an infusion set 106 via flexible tubing 108.

Figure 8:
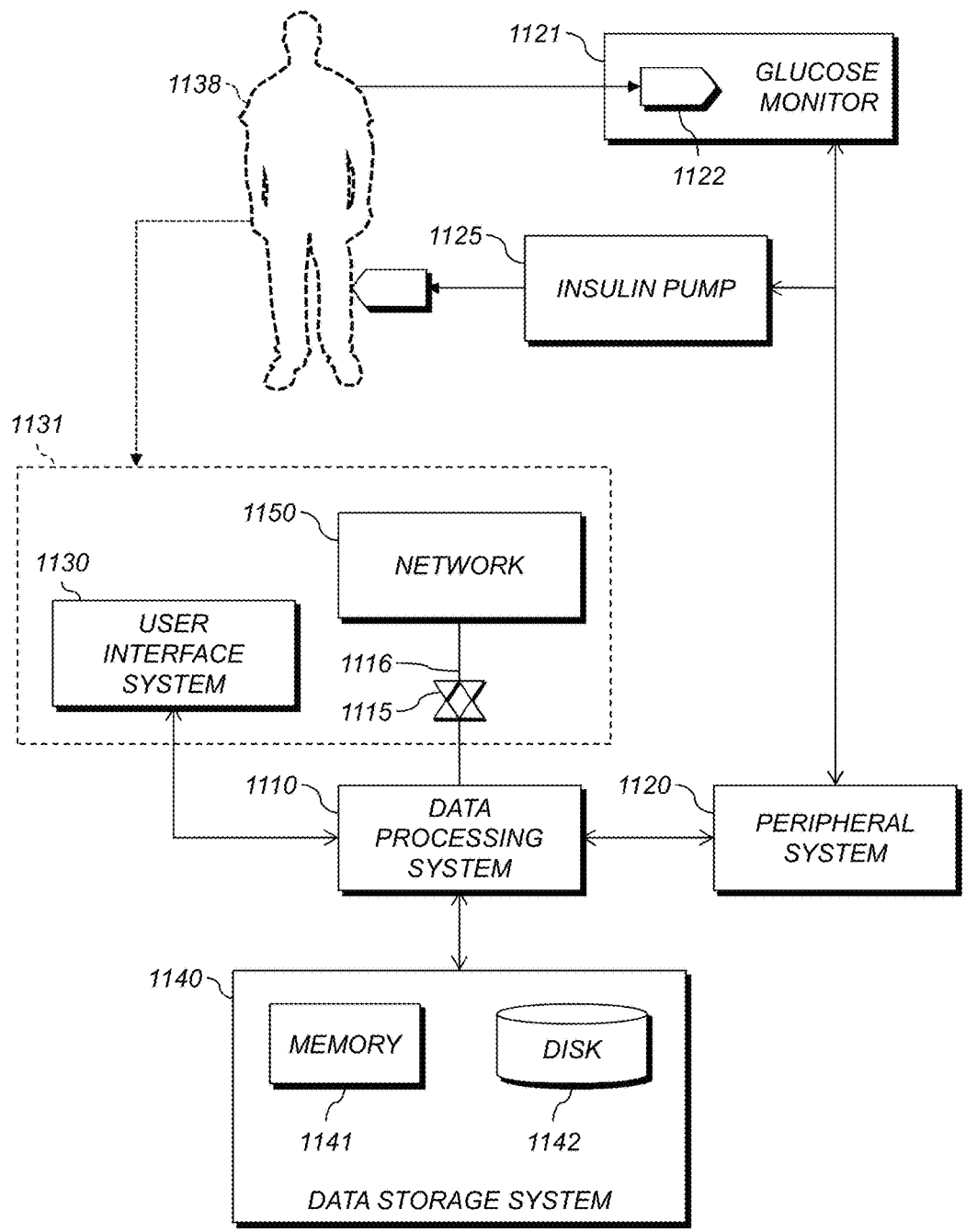
FIG. 8 shows various embodiments of apparatus for the delivery of insulin.

Drug delivery device 102 is configured to transmit and receive data to and from remote controller 104 by, for example, radio frequency communication 110. Drug deliver device 102 may also function as a stand-alone device with its own built in controller. In one embodiment, drug delivery device 102 is an insulin infusion device and remote controller 104 is a hand-held portable controller. In such an embodiment, data transmitted from drug delivery device 102 to remote controller 104 may include information such as, for example, insulin delivery data, blood glucose information, basal, bolus, insulin to carbohydrates ratio or insulin sensitivity factor, to name a few. The controller 104 is configured to include an MPC controller 10 that has been programmed to receive continuous glucose readings from a CGM sensor 112. Data transmitted from remote controller 104 to insulin delivery device 102 may include glucose test results and a food database to allow the drug delivery device 102 to calculate the amount of insulin to be delivered by drug delivery device 102. Alternatively, the remote controller 104 may perform basal dosing or bolus calculation and send the results of such calculations to the drug delivery device. In an alternative embodiment, an episodic blood glucose meter 114 may be used alone or in conjunction with the CGM sensor 112 to provide data to either or both of the controller 104 and drug delivery device 102. Alternatively, the remote controller 104 may be combined with the meter 114 into either (a) an integrated monolithic device; or (b) two separable devices that are dockable with each other to form an integrated device. Each of the devices 102, 104, and 114 has a suitable micro-controller (not shown for brevity) programmed to carry out various functionalities. Examples of micro-controllers that can be used are discussed below with reference to data processing system 1110 (FIG. 8).

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer 126, a server 128 to a memory storage, a personal digital assistant, a mobile telephone, a hospital base monitoring station or a dedicated remote clinical monitoring station.

Drug delivery device 102 includes electronic signal processing components including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing a insulin from a insulin reservoir (e.g., a insulin cartridge) through a side port connected to an infusion set 108/106 and into the body of the user.

Glucose levels or concentrations in physiological fluid (e.g., blood, saliva, or interstitial fluid) of a user can be determined by the use of the CGM sensor 112. The CGM sensor 112 utilizes amperometric electrochemical sensor technology to measure glucose with three electrodes operably connected to the sensor electronics and are covered by a sensing membrane and a biointerface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$. Accordingly, a raw signal may be produced that is representative of the concentration of glucose in the user's body, and therefore may be utilized to estimate a meaningful glucose value. Details of the sensor and associated components are shown and described in U.S. Pat. No. 7,276,029, which is incorporated by reference herein as if fully set forth herein this application. In one embodiment, a continuous glucose sensor from the Dexcom Seven System® (manufactured by Dexcom Inc.) can also be utilized with the exemplary embodiments described herein.

In one embodiment of the invention, the following components can be utilized as a system for management of diabetes that is akin to an artificial pancreas: OneTouch Ping® Glucose Management System by Animas Corporation that includes at least an infusion pump and an episodic glucose sensor; and DexCom® SEVEN PLUS® CGM by DexCom Corporation with interface to connect these components and programmed in the MATLAB® language and accessory hardware to connect the components together; and control algorithms in the form of an MPC that regulates the rate of insulin delivery based on the glucose level of the patient, historical glucose measurement and anticipated future glucose trends, and patient specific information.

Figure 2:
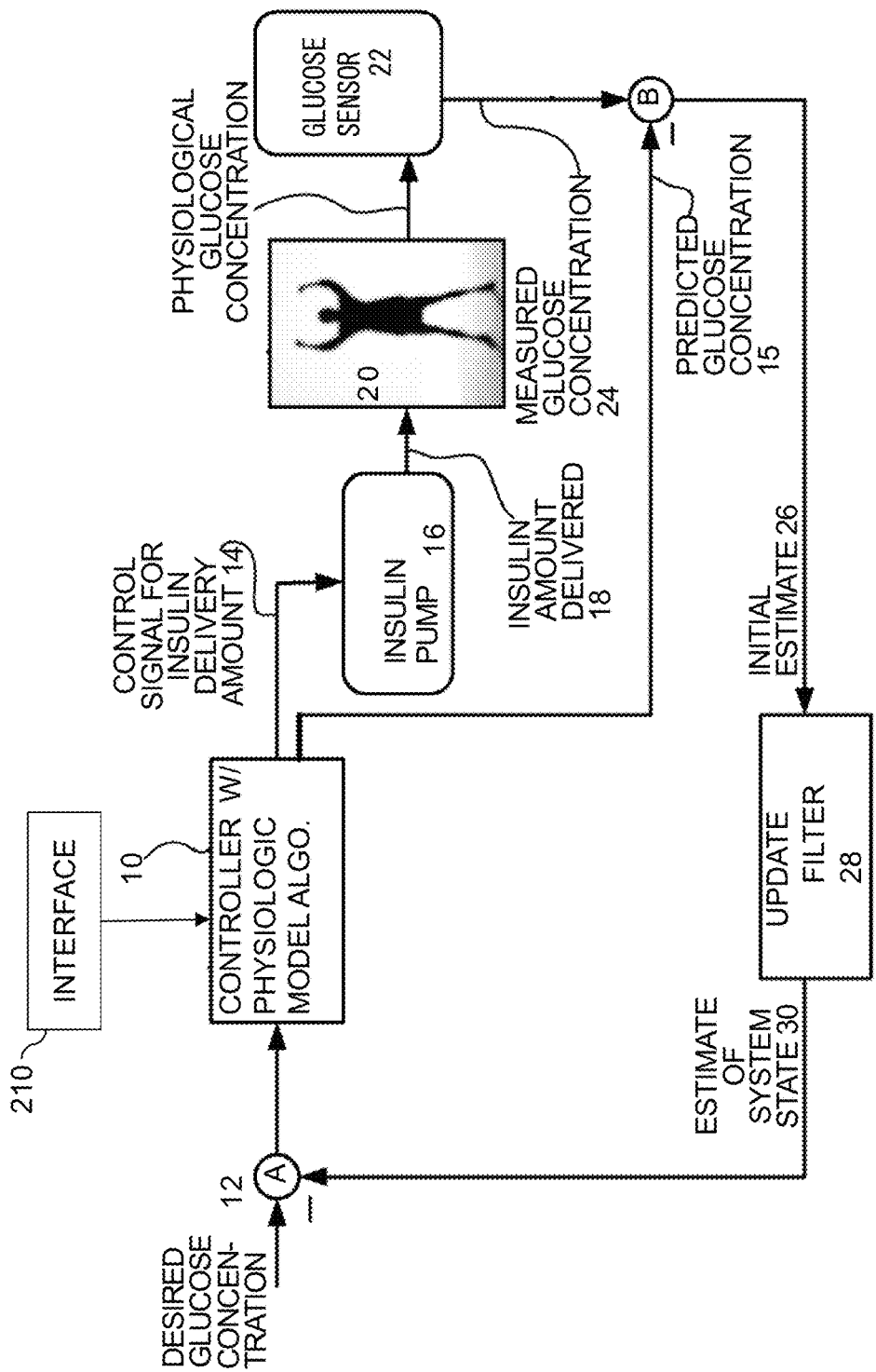
FIG. 2 is a schematic of a control system for managing blood glucose using an insulin pump.

FIG. 2 is a schematic of a control system according to various embodiments for managing blood glucose using an insulin pump. In particular, FIG. 2 provides for an MPC programmed into a control logic module 10 that is utilized in controller 104 (FIG. 1). MPC logic module 10 receives a desired glucose concentration or range of glucose concentration 12 (along with any modification from an update filter 28 so that it is able to maintain the output (i.e., glucose level) of the subject within the desired range of glucose levels.

Referring to FIG. 2, the first output 14 of the MPC-enabled control logic 10 can be a control signal to an insulin pump 16 to deliver a desired quantity of insulin 18 into a subject 20 at predetermined time intervals, which can be indexed, e.g., every 5 minutes using time interval index k. A second output in the form of a predicted glucose value 15 can be utilized in control junction B. A glucose sensor 22 (or 112 in FIG. 1) measures the glucose levels in the subject 20 in order to provide signals 24 representative of the actual or measured glucose levels to control junction B, which takes the difference between measured glucose concentration 24 and the MPC predictions of that measured glucose concentration. This difference provides input for the update filter 26 of state variables of the model. The difference 26 is provided to an estimator (also known as an update filter 28) that provides for estimate of state variables of the model that cannot be measured directly. The update filter 28 is preferably a recursive filter in the form of a Kalman filter with tuning parameters for the model. The output of the update or recursive filter 28 is provided to control junction A whose output is utilized by the MPC in the control logic 10 to further refine the control signal 14 to the pump 16 (or 102 in FIG. 1). A tuning factor can be used with the MPC controller 10 to "tune" the controller in its delivery of the insulin, as discussed below. In various aspects, signals from interface 210 are used by MPC controller 10, as will be discussed. Interface 210 can include one or more touch-screens, buttons, network connections, keyboards, pointing devices, or other devices for receiving data or instructions from humans (e.g., subjects or medical professionals) or other computer systems.

The MPC logic used in controller 10 controls a subject glucose level to a safe glucose zone, e.g., with the lower blood glucose limit of the zone varying between 80-100 mg/dL or set to 90 mg/dL and the upper blood glucose limit varying between about 140-180 mg/dL or set to 180 mg/dL; the algorithm will henceforth be referred to as the "zone MPC". Controlling to a target zone is, in general, applied to controlled systems that lack a specific set point with the controller's goal being to keep the controlled variable, (CV), for example the glucose values, in a predefined zone. Control to a desired, normal-blood-sugar-level ("euglycemic") zone as opposed to a single aim level is highly suitable for the artificial pancreas because of the absence of a natural glycemic set point. Moreover, an inherent benefit of control to zone is the ability to limit pump actuation/activity in a way that if glucose levels are within the zone then no extra correction shall be suggested.

In real-time, the insulin delivery rate $I_D$ from the zone MPC law is calculated by an on-line mathematical optimization (e.g., an operation to find minima or maxima of a function), which evaluates at each sampling time the next insulin delivery rate. The optimization at each sampling time is based on the estimated metabolic state (plasma glucose, subcutaneous insulin) obtained from the dynamic model stored in module 10.

The MPC of control logic 10 incorporates an explicit model of human T1DM glucose-insulin dynamics. The model is used to predict future glucose values and to calculate future controller moves that will bring the glucose profile to the desired range. MPC in controllers can be formulated for both discrete- and continuous-time systems; the controller is set in discrete time, with the discrete time (stage) index k referring to the epoch of the $k^{th}$ sample occurring at continuous time $t=k \cdot T_s$, where $T_s=5$ min is the sampling period. Software constraints ensure that insulin delivery rates are constrained between minimum (i.e., zero) and maximum values. The first insulin infusion (out of N steps) is then implemented. At the next time step, k+1 based on the new measured glucose value and the last insulin rate, the process is repeated.

Specifically, we start with the original linear difference model used for zone MPC:

$$G'(k)=a_1G'(k-1)+a_2G'(k-2)+a_3G'(k-3)+a_4G'(k-4)+a_5G'(k-5)+bI_M(k-4)I_M(k)=c_1I_M(k-1)+c_2I_M(k-2)+d_1I'_D(k-1)+d_2I'_D(k-2) \quad (1)$$

where:
  k is the discrete time interval index having a series of indexing counters where k=1, 2, 3 . . .
  G' is the measured glucose concentration
  $I_M$ is the "mapped insulin" which is not a measured quantity
  $I'_D$ is the delivered insulin or a manipulated variable
  and coefficients $a_1$~2.993; $a_2$~(−3.775); $a_3$~2.568; $a_4$~(−0.886); $a_5$~0.09776; b~(−1.5); $c_1$~1.665; $c_2$~(−0.693); $d_1$~0.01476; $d_2$~0.01306.

Using an FDA-accepted metabolic simulator, as known to those skilled in the art, Eq. (1) can be reduced to the following linear difference model in Equation (2):

$$G'(k) = 2.993G'(k-1) - 3.775G'(k-2) + \qquad (a)$$
$$2.568G'(k-3) - 0.886G'(k-4) + 0.09776G'(k-5) -$$
$$1.5I_M(k-4) + 0.1401\,Meal_M(k-2) + 1.933\,Meal_M(k-3)$$

$$I_M(k) = 1.665 I_M(k-1) - 0.693 I_M(k-2) + \qquad (b)$$
$$0.01476\,I'_D(k-1) + 0.01306\,I'_D(k-2)$$

$$Meal_M(k) = 1.501\,Meal_M(k-1) + 0.5427\,Meal_M(k-2) + \qquad (c)$$
$$0.02279\,Meal(k-1) + 0.01859\,Meal(k-2)$$

(2)

where:
  G' is the glucose concentration output (G) deviation variable (mg/dL), i.e., G'≡G−110 mg/dL,
  $I_D$' is the insulin infusion rate input ($I_D$) deviation variable (U/h), i.e., $I_D$'≡$I_D$−basal U/h,
  Meal is the CHO ingestion input (gram-CHO),
  $I_M$ is the mapped subcutaneous insulin infusion rates (U/h), and
  $Meal_M$ is the mapped CHO ingestion input (gram-CHO).

The dynamic model in Eq. (2) relates the effects of insulin infusion rate ($I_D$), and CHO ingestion input (Meal) on plasma glucose. The model represents a single average model for the total population of subjects. The model and its parameters are fixed.

The second-order input transfer functions described by parts (b) and (c) in Eq. (2) are used to generate an artificial input memory in the zone MPC schema to prevent insulin over-dosing, and consequently prevent hypoglycemia. In order to avoid over-delivery of insulin, the evaluation of any sequential insulin delivery must take into consideration the past administered insulin against the length of the insulin action. However, a one-state linear difference model with a relatively low order uses the output (glycemia) as the main source of past administered input (insulin) "memory." In the face of the model mismatch, noise, or change in the subject's insulin sensitivity, this may result in under- or over-delivery of insulin. This is mitigated by adding two additional states ($I_M$ and $Meal_M$) for the mapped insulin and meal inputs that carry a longer insulin memory.

Zone MPC is applied when the specific set point value of a controlled variable (CV) is of low relevance compared to a zone that is defined by upper and lower boundaries. Moreover, in the presence of noise and model mismatch there is no practical value using a fixed set point. Other details of the derivation for the Zone MPC technique are shown and described in Benyamin Grosman, Ph.D., Eyal Dassau, Ph.D., Howard C. Zisser, M. D., Lois Jovanovič, M. D., and Francis J. Doyle III, Ph.D. "Zone Model Predictive Control: A Strategy to Minimize Hyper and Hypoglycemic Events" Journal of Diabetes Science and Technology, Vol. 4, Issue 4, July 2010, and US Patent Application Publication No. 2011/0208156 to Doyle et al., entitled "Systems, Devices, and Methods to Deliver Biological Factors or Drugs to a Subject," with the publication date of Aug. 25, 2011, all which are incorporated by reference as if set forth herein with a copy in the Appendix. Additional details of the Zone MPC are shown and described in US Patent Application Publication No. 20110208156, which is incorporated by reference as if set forth herein with a copy in the Appendix. A related derivation of zone MPC was presented in Maciejowski J M., "Predictive Control with Constraints" Harlow, UK: Prentice-Hall, Pearson Education Limited, 2002.

Zone MPC typically divides the range of the controlled variable into three different zones. The permitted range is the control target and it is defined by upper and lower bounds. The upper, hyperglycemic zone represents undesirably-high predicted glucose levels. The lower, hypoglycemic or low alarm zone represents undesirably-low predicted glycemic values. The lower zone can be a hypoglycemic zone or a low alarm zone, which is a pre-hypoglycemic protective zone. The zone MPC optimizes the predicted glycemia by manipulating the near-future insulin control moves to stay in the permitted zone under specified constraints. The predicted residuals are defined as the difference between the CV that is out of the desired zone and the nearest bound.

In various aspects, zone MPC is implemented by defining fixed upper and lower bounds as soft constraints. A mathematical optimization process uses weights that switch between zero and some final values when the predicted CVs are in or out of the desired zone, respectively.

Model predictive control operates by mathematically minimizing a cost function. For example, future glucose levels are predicted from past glucose levels and insulin amounts and from the candidate insulin amounts to be delivered in the future, e.g., using linear difference models of insulin-glucose dynamics. A cost is assigned to these predicted glucose levels. For zone MPC, the cost function defines the zone of control by setting cost much lower (e.g., 0) within the zone than out of the zone. Therefore, the cost of future glucose levels causes the optimization to select future $I_D$' values that will tend to keep the predicted outputs within the zone of control (e.g., a zone defined by upper and lower bounds), rather than future values that will move the predicted outputs towards a specific set point. Optimizing using such a cost function can reduce hypo- and hyperglycemic excursions from the zone of control. The aggressiveness of the controller in reducing excursions is influenced by the cost function, e.g., weights contained therein.

The zone MPC cost function J is:

$$J(I'_D) = Q \cdot \sum_{j=1}^{P} \|G^{zone}(k+j)\| + R \cdot \sum_{j=0}^{M-1} \|I'_D(k+j)\| \qquad (3)$$

s.t.

$$G(k+j) = f[G(k+j-1), I'_D(k+j-1)] \quad \forall\, j = 1, P$$
$$-basal(k+j) \le I'_D(k+j) \le 72 \quad \forall\, j = 0, M-1$$

In various embodiments, $I_D$' is expanded:

$$J(I_D') = \Sigma\|G^{zone}(k+j)\| + R \cdot \Sigma \|I_D(k+j) - basal(k+j)\| \qquad (4)$$

where:
  Q is a weighting factor on the predicted glucose term;
  R is a tuning factor on the future proposed inputs in the cost function;

$f$ is the prediction function (in Eq. (2));

vector $I_D$ contains the set of proposed near-future insulin infusion amounts. It is the "manipulated variable" because it is manipulated in order to find the minimum in J;

basal(t) is the basal delivery rate at time interval t; and $G^{zone}$ is a variable quantifying the deviation of future model-predicted CGM values G outside a specified glycemic zone. In various embodiments, $G^{Zone}$ is:

$$G^{zone} = \begin{cases} 0 & \text{if } G_{ZL} \leq G \leq G_{ZH} \\ G - G_{ZH} & \text{if } G > G_{ZH} \\ G_{ZL} - G & \text{if } G < G_{ZL} \end{cases} \quad (5)$$

where the glycemic zone is defined by the upper limit $G_{ZH}$ and the lower limit $G_{ZL}$.

Thus, if all the predicted glucose values are within the zone, then every element of $G^{zone}$ is equal to 0, and consequently J is minimized with $I_D$=basal for that time of day, i.e., the algorithm "defaults" to the patient's current basal insulin infusion rate. On the other hand, if any of the predicted glucose values are outside the zone, then $G^{zone}>0$ and thus contributes to the cost function. In this case, the near-future proposed insulin infusion amounts $I_D$ will deviate from the basal in order to prevent out-of-zone deviation in $G^{zone}$ from ever happening, which will also "contribute" to the cost function. Then, a quantitative balance is found in the optimization, based on the weighting factor R.

In order to solve optimization problem of Equations (2)-(5), a commercially available software (e.g., MATLAB's "fmincon.m" function) can be used. For this function, the following parameters are used for each optimization:

Initial guess for the insulin delivery rates, $I_D'(0)$, is the null vector $\vec{0} \in R^M$, e.g., if M=5 the initial guess for each optimization is $I_D'$=[0 0 0 0 0]. This implies that the initial guess is equivalent to the basal rate.

Maximum number of function evaluations allowed is Max_f=100*M, where M is control horizon as described earlier.

Maximum number of iterations is Max_i=400, which is fixed.

Termination on the cost function values Term_cost=1e-6, which is fixed.

Termination tolerance Term_tol on the manipulated variables $I_D'$ is 1e-6.

The following hard constraints are implemented on the manipulated variables $I_D'(t)$:

$$-basal(t) \leq I_D'(t) \leq 72 \text{ U/h} \quad (6)$$

where basal is the subject's basal rate as set by the subject or his/her physician, e.g., in the range 0.6-1.8 U/hr.

Although the values of control horizontal parameter M and prediction horizon parameter P have significant effects on the controller performance, and are normally used to tune an MPC based controller, they can be heuristically tuned based on knowledge of the system. Tuning rules are known to those skilled in the field. According to these rules M and P may vary between:

$$2 \leq M \leq 10$$

$$20 \leq P \leq 120. \quad (7)$$

In Various Embodiments, M=5 and P=108.

The ratio of the output error weighting factor Q and the input change weighting matrix or tuning factor R may vary between:

$$10 \leq \frac{R}{Q} \leq 1000 \quad (8)$$

In various embodiments, R/Q=500 or 250.

Once the controller is initialized and switched on, real-time calculations take place every five minutes, corresponding to the sample time for the glucose sensor. The first element of $I_D$ is delivered as an insulin dose to the patient through the insulin pump, five minutes elapse, a new CGM reading becomes available, and the process repeats. In various aspects, the controller delivers the basal rate until M samples have been taken; this is sometimes referred to as a "burn-in" period. It is noted that the future control moves are hard-constrained, set by the insulin pump's ability to deliver a maximum rate of insulin and the inability to deliver negative insulin values. Other details of related subject matter including state estimator, and other MPC are provided by Rachel Gillis et al., "*Glucose Estimation and Prediction through Meal Responses Using Ambulatory Subject Data for Advisory Mode Model Predictive Control*" Journal of Diabetes Science and Technology Vol. 1, Issue 6, November 2007 and by Youqing Wang et al., "*Closed-Loop Control of Artificial Pancreatic β-Cell in Type* 1 *Diabetes Mellitus Using Model Predictive Iterative Learning Control*" IEEE Transactions on Biomedical Engineering, Vol. 57, No. 2, February 2010, which are hereby incorporated by reference into this application as if fully set forth herein.

It is known that the tuning parameter (designated here as "R") can have a significant effect on the quality of the glucose control. The parameter—known as the aggressiveness factor, gain, and other names—determines the speed of response of the algorithm to changes in glucose concentration. A relatively conservative value of R results in a controller that is slow to adjust insulin infusion amounts (relative to basal) in response to changes in glucose; on the other hand, a relatively aggressive value of R results in a controller that is quick to respond to changes in glucose. In principle, an aggressive controller would result in the best glucose control if 1) the available glucose measurements are accurate, and moreover 2) the model predictions of future glucose trends are accurate. If these conditions are not true, then it may be safer to use a conservative controller.

In various aspects, basal rate basal(t) changes over time. For example, the basal rate can be lower at night (e.g., 0.5 U/h), when metabolism is low, and higher during the day. The cost function J above includes an $I_D$—basal term, so there is a cost to deviating from basal. The Zone MPC controller is driven to keep $I_D$ close to basal unless doing so raises the $G^{zone}$ term in J more than a deviation from basal would.

Normally, MPC-controlled insulin pumps deliver insulin according to a base insulin delivery profile (basal(t)), suitably adjusted to maintain glucose within the euglycemic zone as described above. Described herein are three examples of temporary insulin delivery profiles patients can use to tune their insulin supply without requiring extensive hand computations, and without concern for a hypo- or hyperglycemic excursion. These examples are referred to as "soft," "semi-soft," and "hard." These three can be used together or separately, and features of the various embodiments herein can be combined. These aspects can be used to provide temporary basals or extended boluses, or extended boluses contemporaneously with temporary basals. In various aspects, an insulin-pump controller operates at any given time with one of a base, soft, semi-soft, or hard insulin delivery profile; the profiles are not used simultaneously in these aspects.

Figure 3:
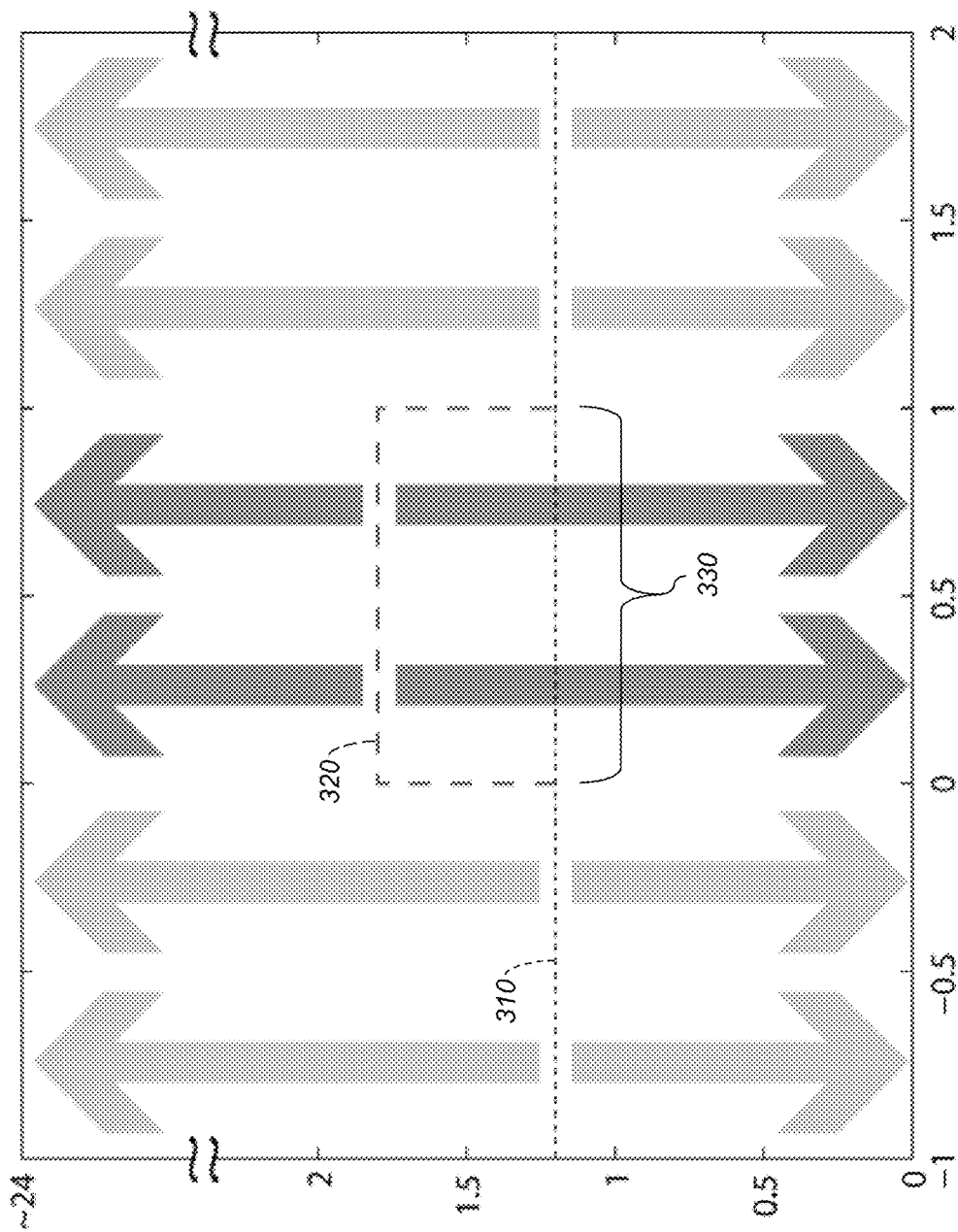
FIGS. 3 and 4 are examples of insulin delivery profiles according to various aspects.

FIG. 3 shows an example of a soft temporary insulin delivery profile. The abscissa is time, e.g., in hours, from the beginning of the temporary insulin delivery profile (t=0). The ordinate is insulin delivery rate in U/h. Note that the ordinate is in the physical units of U/h, and thus 0 on the ordinate means no insulin (as opposed to deviation units, which would mean that 0 is actually the basal rate). Other units can be used for either axis, and the ranges of values shown on each axis are not limiting. This is also the case for FIGS. 4 and 6.

Base insulin delivery profile 310 is an example of a basal function that specifies constant insulin delivery. In this example, the patient's base insulin delivery rate is 1.2 U/h. The temporary insulin delivery profile 320 (dashed line) specifies the base insulin delivery profile plus 50%, or 1.8 U/h, for 1 h, starting at time zero. Therefore, in the time range 330 between times 0 and 1 h on this figure, basal is 1.8 U/h. Outside time range 330, basal is 1.2 U/h. The value of basal at a time interval k is the base insulin delivery profile value at time k outside the time range 330, or the temporary insulin delivery profile value inside the time range 330. The temporary insulin delivery profile can be received directly, or can be produced by modifying the base insulin delivery profile value according to a received profile modifier.

Continuing this example, although basal is higher in the 0 . . . 1 h time range 330 than outside it, the zone MPC controller module is not required to increase delivery in the time range 330. The $I_D$ amount computed depends on values of the cost function J. In general, as long as the predicted glucose level is within the MPC zone [$G_{zL}$, $G_{ZH}$], J will be lowest when $I_D$ follows basal, which is the temporary insulin delivery profile inside time range 330. Therefore, the temporary insulin delivery profile is likely to recommend higher-than-base insulin amounts for at least part of the time range 330. However, if the predicted glucose level exits the zone, the MPC algorithm will select whatever $I_D$ values are necessary to bring glucose back into the zone. This is represented graphically by the block arrows: the controller has the full range of possible $I_D$ values available whether inside or outside time range 330.

Patients might, for example, program soft temporary basals or soft extended boluses if they believe they will need an atypical amount of insulin in the near future but are not sure how much. Soft delivery profiles provide confidence that zone controllers will still act to protect patients from glycemic excursions.

Figure 4:
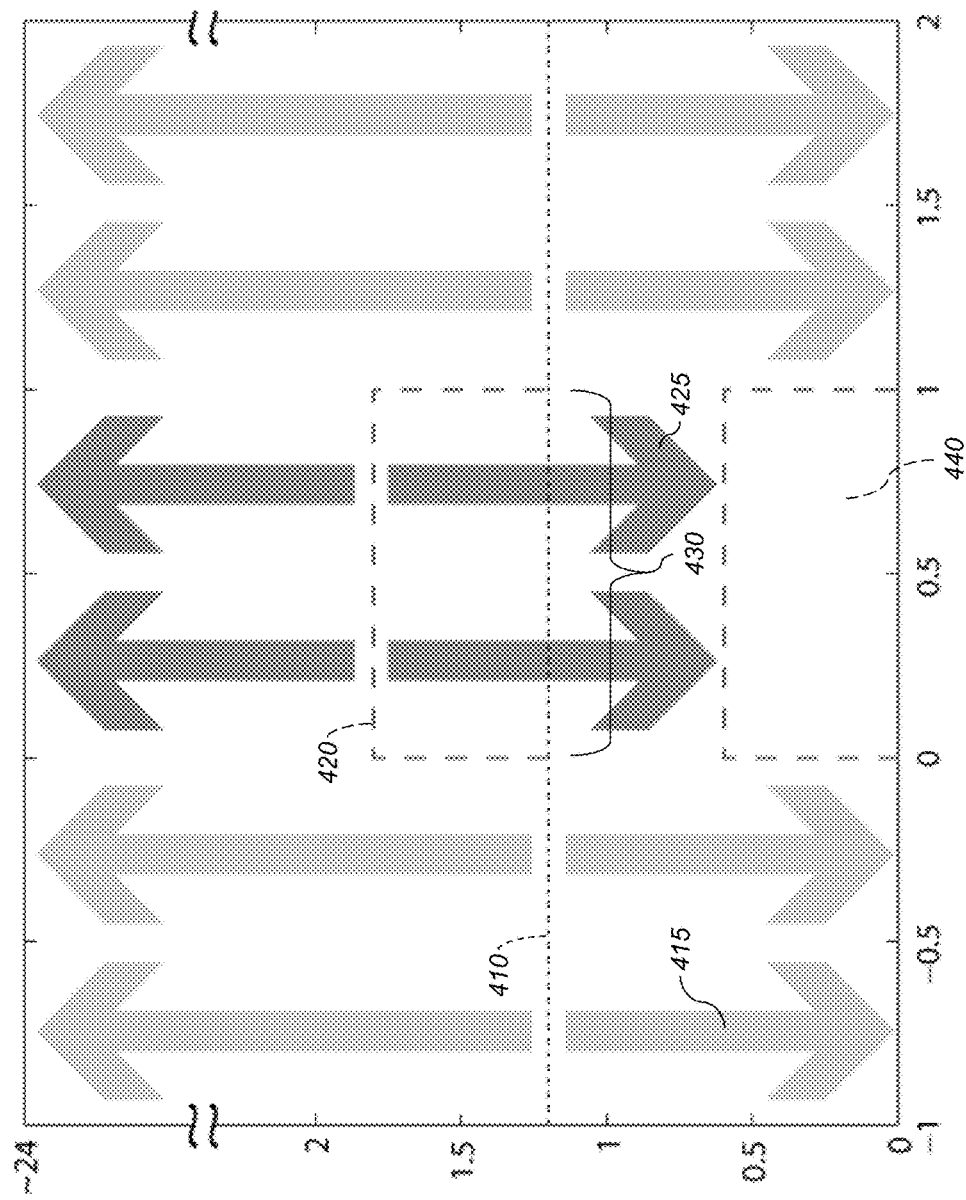

FIG. 4 shows an example of a "semi-soft" or "hybrid" temporary insulin delivery profile. The base insulin delivery profile 410 in this example is 1.2 U/h. As in the example of FIG. 3, the temporary insulin delivery profile 420 (dashed line), which corresponds to the application of a temporary basal or extended bolus, specifies 50% over base profile 410, or 1.8 U/h, in time range 430 (0-1 h). Outside time range 430, the controller can specify any amount $I_D$ of insulin, down to zero, as represented by the block arrows 415. Inside time range 430, the controller module is constrained to recommend at least the additional programmed insulin (temporary minus base), but can deliver more as it sees fit. This range of possible $I_D$ values is represented by block arrows 425. Region 440 is empty, indicating that the zone controller cannot select an $I_D$ value in this range during this time. Region 440 can be kept empty by constraining $I_D$ for the present time interval to be no less than temporary minus base, implemented by adjusting Eq. (6) appropriately.

In various aspects, if the additional programmed amount $$\Delta(t)=(\text{temporary}-\text{base})$$

is too much insulin, driving the blood glucose down, a safety module can reduce this dose in order to reduce the probability or severity of a hypoglycemic excursion. In other aspects, safety modules are not required because of patient biochemistry or other factors. Safety modules are discussed further below.

In an example, patients might program semi-soft temporary basals or semi-soft extended boluses if they believe they will need some additional insulin to offset anticipated carbohydrate intake, e.g., at a cocktail party. The MPC controller will still provide more insulin as necessary to reduce the probability of a hyperglycemic excursion, and can reduce insulin subject to the $\Delta(t)$ limit to reduce the probability of a hypoglycemic excursion.

In various examples, the temporary insulin delivery profile is used to provide an extended bolus. The temporary insulin delivery profile includes former and latter subranges of the selected time range and specifies higher amounts or rates of insulin delivery in the former subrange than in the latter subrange. For example, instead of a 10 U bolus administered at t=0, 5 U can be administered immediately and 5 U over the remainder of an hour. The first 5 U are administered starting from t=0 for as long as the pump takes to deliver 5 U. If the pump is limited to a maximum delivery rate of 1 U/min., the first 5 U will take 5 min. The period from t=0 to 5 min is the former subrange. The remaining 5 U of the bolus are spread over remainder of an hour, i.e., from t=5 min to 60 min. This time range is the latter subrange. The delivery rate in the latter subrange is thus 0.091 U/min, much less than the 1 U/min rate in the first subrange. Each subrange can be continuous or include multiple separated segments of time.

Figure 5:
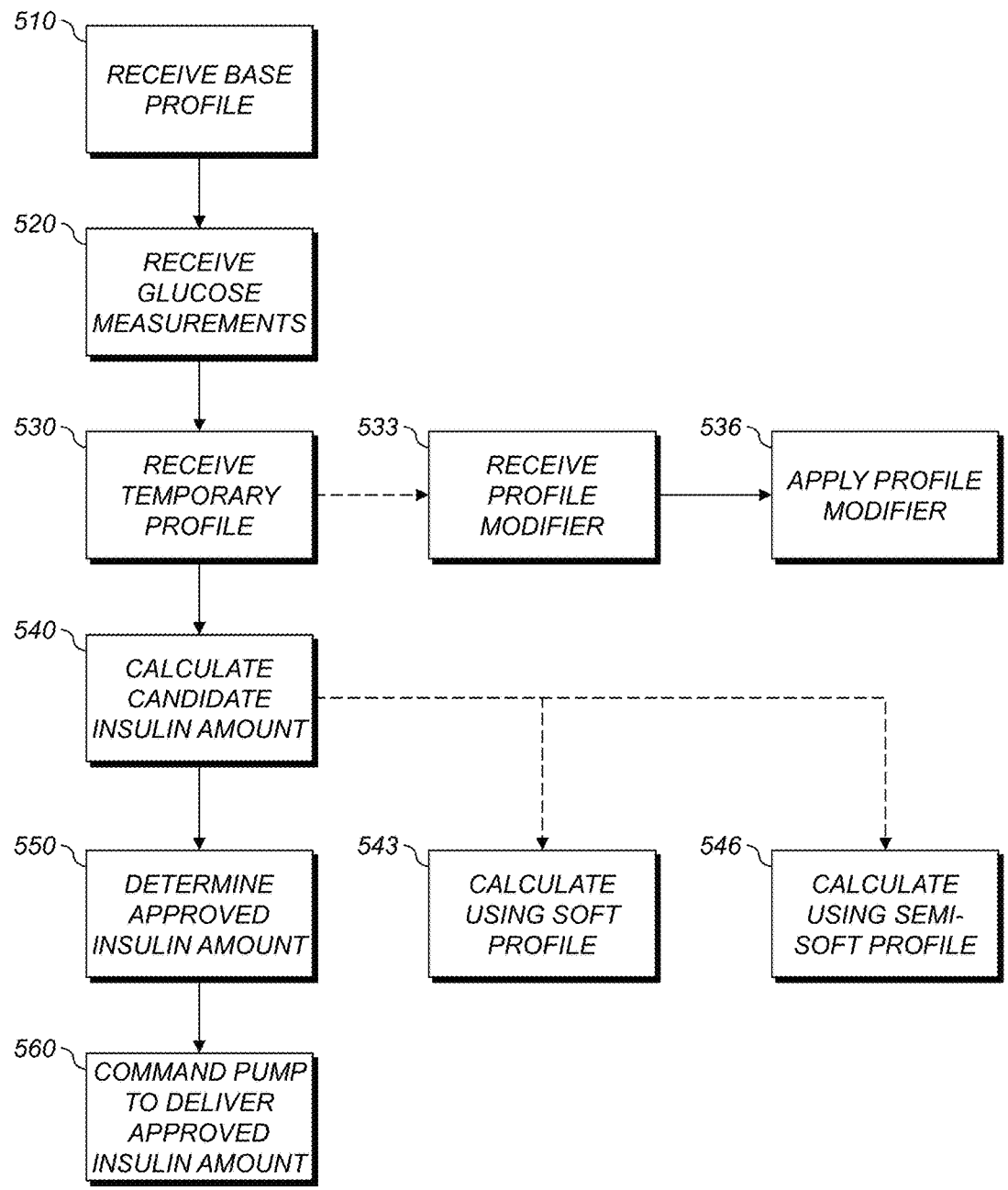
FIG. 5 is a flowchart illustrating exemplary methods of controlling an infusion pump.

FIG. 5 is a flowchart illustrating exemplary methods of controlling an infusion pump. Various aspects shown here implement soft or semi-soft control schemes. Solid arrows connect subsequent steps and dashed arrows connect steps to their substeps. The infusion pump (e.g., insulin pump 16, FIG. 2) is responsive to a controller (e.g., controller 10, FIG. 2) that receives data from at least one glucose sensor (e.g., glucose sensor 22). In various embodiments, the steps of the method are automatically performed using the controller. Processing begins with step 510.

In step 510, a base insulin delivery profile is received. As discussed above, the base profile (e.g., profile 410, FIG. 4) is not always basal(k) as used in the Zone MPC algorithm. Step 510 is followed by step 520, but can be performed simultaneously or after step 520.

In step 520, the controller receives one or more respective glucose level measurements for each time interval of a series of discrete time intervals. The measurements are received from the glucose sensor(s). The measurements can be measurements of a patient or subject, e.g., a human. The time intervals can be evenly spaced or not, and can skip in the middle. Step 520 is followed by step 530.

In step 530, a temporary insulin delivery profile is received. The temporary profile extends over a selected time range of the time intervals. The range does not have to be continuous and can include separated subranges. Step 530 is followed by step 540.

In step 540, the controller calculates a candidate insulin delivery amount for a selected one of the time intervals based on a model predictive controller. The model predictive controller, e.g., as discussed above, predicts an excursion of the glucose level from a selected target glucose range (e.g., $G^{zone}(k+j)$) using at least some of the glucose measurements, and optionally using estimates of a metabolic state of the subject. The model predictive controller then computes an estimated insulin delivery amount (e.g., $I_D$). In various examples, determining the estimated insulin delivery amount includes making an initial guess of $I_D$:=basal, as discussed above. The model predictive controller then adjusts the estimated insulin delivery amount, e.g., by mathematical minimization of J, to provide the candidate insulin delivery amount. The adjustment is performed in accordance with the predicted excursion, the base insulin delivery profile, or, if the selected time interval is in the selected range, the temporary insulin delivery profile. Step 540 is followed by step 550.

In step 550, an approved insulin delivery amount is determined from the candidate insulin delivery amount. In an example, the approved amount is set equal to the candidate amount. In another example, a safety module determines the approved amount. Specifically, in this example, the candidate delivery amount is reduced according to a hypoglycemia safety model to provide the approved insulin delivery amount. The hypoglycemia safety model can be the glucose model used by the model predictive controller, or can be a different model. If the hypoglycemic safety model indicates the candidate insulin delivery amount will not lead to hypoglycemia, the candidate insulin delivery amount is approved unchanged, i.e., with a reduction of zero (0). If the hypoglycemic safety model indicates the candidate insulin delivery amount may lead to hypoglycemia, the candidate insulin delivery amount is reduced to an amount that does not lead to hypoglycemia according to the hypoglycemic safety model. In various aspects, the Safety Supervision Model from the University of Virginia can be used. Step 550 is followed by step 560.

In step 560, the controller commands the infusion pump to deliver the approved insulin delivery amount. In this way, insulin can be delivered to a patient to maintain the patient's blood glucose within the desired glycemic zone.

The temporary insulin profile can be provided as new amounts, or as changes to existing amounts in the base insulin delivery profile. For example, in various embodiments, step 530 of receiving a temporary insulin delivery profile includes step 533 of receiving a profile modifier. The profile modifier can be, e.g., +1 U/h or +50%. Step 533 is followed by step 536, in which the profile modifier is applied to the base insulin delivery profile to produce the temporary insulin delivery profile. Application can include adding or multiplying the profile modifier with values of the base insulin delivery profile (e.g., 1 U/h+0.5 U/h, or 1 U/h*150%). The temporary insulin profile can also be provided as changes to existing amounts in the base insulin delivery profile as modified by a prior-applied temporary insulin delivery profile. For example, in a given time interval k, a first-applied temporary insulin delivery profile can specify +50% insulin. Additionally, a second-applied temporary insulin delivery profile, e.g., for an extended bolus, can specify +0.5 U/h. The insulin delivery for time interval k is then (base(k)×1.5)+0.5 for base insulin delivery profile base(k).

In various aspects, a soft profile is used. Specifically, step 540 includes step 543. In step 543, if the selected time interval is in the selected range (e.g., time range 330, FIG. 3), the estimated delivery amount is adjusted in accordance with the predicted excursion and the temporary insulin delivery profile. If the selected time interval is not in the selected range, the estimated delivery amount is adjusted in accordance with the predicted excursion and the base insulin delivery profile. The controller can have the full range of adjustment available, but using different profiles, i.e., different basal(k) values, inside versus outside the selected time range.

In other aspects, a semi-soft profile is used, and step 540 includes step 546. In step 546, if the selected time interval is in the selected range (e.g., time range 430, FIG. 4), the estimated delivery amount is adjusted in accordance with the predicted excursion and the temporary insulin delivery profile. The calculated insulin delivery amount at time t is constrained to be at least a difference $\Delta(t)$ between the temporary insulin delivery profile and the base insulin delivery profile in the selected time interval, e.g., estimated:=max(estimated,$\Delta(t)$).

If the selected time interval is not in the selected range, the estimated delivery amount is adjusted in accordance with the predicted excursion and the base insulin delivery profile.

Figure 6:
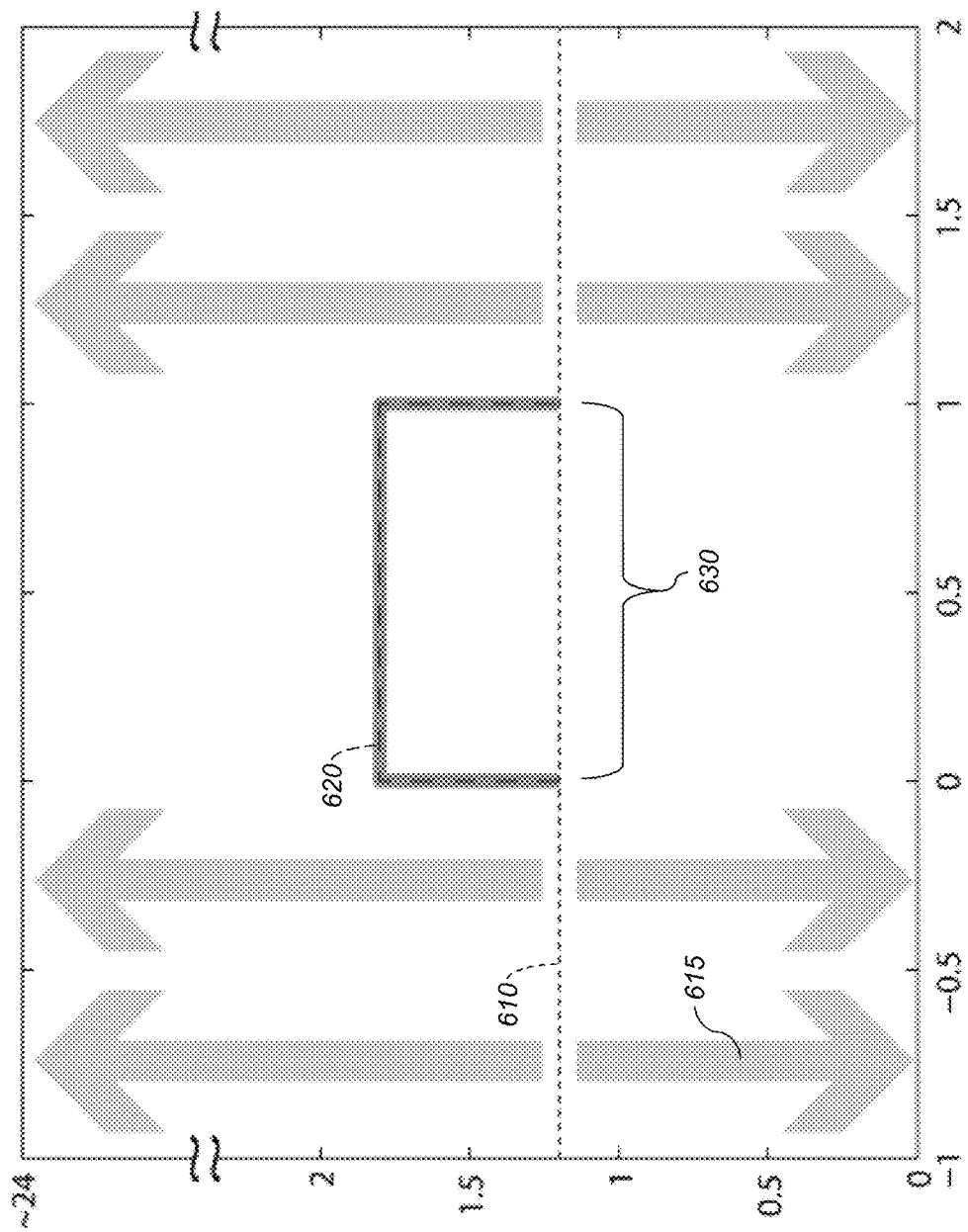
FIG. 6 is an example of insulin delivery profiles according to various aspects.

FIG. 6 shows an example of a "hard" temporary basal or extended bolus. The base insulin delivery profile 610 specifies a rate of 1.2 U/h. The hard temporary insulin delivery profile 620 is 50% higher, or 1.8 U/h, for 1 h, starting at time zero (time range 630). Before and after time range 630, the controller module can recommend delivery away from the base insulin delivery profile 610 as necessary to maintain blood glucose level within the zone. This is represented graphically by block arrows 615. During time range 630, the controller module simply provides the amount of insulin specified in temporary insulin delivery profile 620. As discussed above, in some embodiments, a safety module can reduce insulin dose if necessary. Not all configurations require a safety module.

In an example, a hard temporary basal or extended bolus can be applied if a patient or doctor has determined that a specific insulin amount is required. During a hard temporary insulin delivery profile 620, the controller still measures glucose levels G(k−1, k−2 . . . ) and records the measurements, but the controller does not need to predict glucose levels G(k) unless such prediction is required by a safety module or another processing function. Since all data are available, at the end of the time range 630, normal MPC control of $I_D$ can resume without an M-cycle delay.

Figure 7:
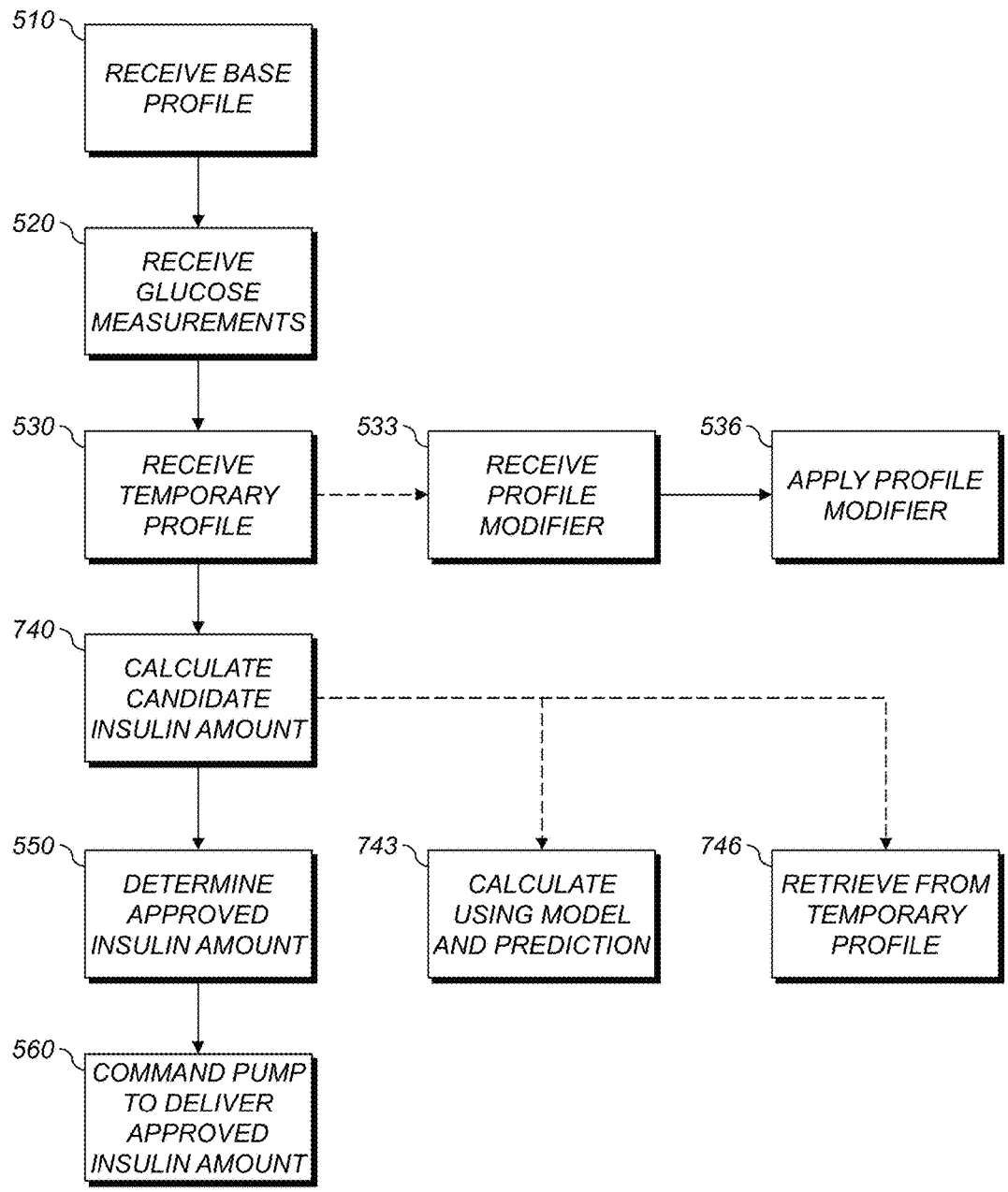
FIG. 7 is a flowchart of ways of controlling an infusion pump according to various aspects.

FIG. 7 is a flowchart illustrating exemplary methods of controlling an infusion pump. Various aspects shown here implement soft or semi-soft control schemes. Solid arrows connect subsequent steps and dashed arrows connect steps to their substeps. The infusion pump (e.g., insulin pump 16, FIG. 2) is responsive to a controller (e.g., controller 10, FIG. 2) that receives data from at least one glucose sensor (e.g., glucose sensor 22). In various embodiments, the steps of the method are automatically performed using the controller. Processing begins with step 510. Steps 510, 520, 530, 533, and 536 can be as shown in FIG. 5. The hard profile is applied very differently than a soft or semi-soft profile. Step 530 is followed by step 740.

In step 740, a candidate insulin delivery amount for a selected one of the time intervals is calculated. A model predictive controller determines whether the selected time interval is outside the selected range (e.g., time range 630, FIG. 6). If so, the model predictive controller predicts an excursion of the glucose level from a selected target glucose range using at least some of the glucose measurements, as discussed above. The model predictive controller computes an estimated insulin delivery amount and adjusts the estimated insulin delivery amount to provide the candidate insulin delivery amount. The adjustment is performed in accordance with the predicted excursion and the base insulin delivery profile. This is represented by sub-step 743.

If the selected time interval is in the selected range, however, the controller or model predictive controller retrieves the candidate insulin delivery amount for the selected time interval from the temporary insulin delivery profile ($I_D(k)$:=basal(k), where basal is the temporary insulin delivery profile or the base insulin delivery profile modified by a profile modifier, as discussed above). This is represented by sub-step 746. Step 740 is followed by step 550.

Steps 550 and 560 can be as shown in FIG. 5: determining an approved insulin delivery amount and commanding the infusion pump to deliver the approved insulin delivery amount. In various embodiments of step 550, as discussed above, a hypoglycemia safety model is used to determine whether a hypoglycemic excursion is predicted and, if so, the candidate delivery amount is reduced to provide the approved insulin delivery amount.

To recap, the system of FIG. 2 is provided to manage diabetes of a subject. In this system, the following components are utilized: continuous glucose sensor 22, pump 16, and controller 10. The continuous glucose monitor continuously measures glucose level of the subject at discrete generally uniform time intervals (indexed "k", e.g., approximately every 30 seconds or every minute, or every five minutes) and provides the glucose level at each interval in the form of glucose measurement data. The insulin infusion pump is controlled by the controller 10 to deliver insulin to the subject 20. The controller 10 is programmed with the appropriate MPC program to control the pump and communicate with the glucose meter and the glucose monitor. In this aspect, the controller determines an insulin delivery rate for each time interval in the time interval index (k) from the model predictive control based on desired glucose concentration 12 and glucose concentration 24 measured by the monitor 22 at each interval of the interval index (k).

FIG. 8 shows various embodiments of apparatus for the delivery of insulin, including data-processing components for analyzing data and performing other analyses and functions described herein, and related components. Subject 1138 is not part of the apparatus but is shown for context. Glucose monitor 1121 is adapted to continually measure respective glucose levels of subject 1138 at discrete time intervals and provide respective glucose measurement data indicating each measured glucose level. Glucose monitor 1121 can include one or more glucose sensor(s) 1122, e.g., including glucose oxidase or glucose dehydrogenase, to transduce glucose concentration to a signal that can be measured electrochemically. Examples of glucose sensors are discussed above. Insulin infusion pump 1125 is configured to deliver insulin, e.g., to subject 1138, in response to a delivery control signal. The apparatus includes a controller, e.g., data processing system 1110, that receives glucose measurement data from the glucose monitor 1121 and commands the pump 1125 to deliver insulin.

A peripheral system 1120, a user interface system 1130, and a data storage system 1140 are communicatively connected to the data processing system 1110. Data processing system 1110 can be communicatively connected to network 1150, e.g., the Internet or an X.25 network, as discussed below.

The data processing system 1110 includes one or more data processor(s) that implement processes of various aspects described herein. A "data processor" is a device for processing data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 1120, user interface system 1130, and data storage system 1140 are shown separately from the data processing system 1110 but can be stored completely or partially within the data processing system 1110.

The data storage system 1140 includes or is communicatively connected with one or more tangible non-transitory computer-readable storage medium(s) configured to store information, including the information needed to execute processes according to various aspects. A "tangible non-transitory computer-readable storage medium" as used herein refers to any non-transitory device or article of manufacture that participates in storing instructions which may be provided to the data processing system 1110 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Aspects of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 1110 to perform a particular series of operational steps when loaded, thereby implementing functions or acts specified herein.

In an example, data storage system 1140 includes memory 1141, e.g., a random-access memory, and disk 1142, e.g., a tangible computer-readable storage device such as a hard drive or a solid-state flash drive. Computer program instructions are read into memory 1141 from disk 1142, or a wireless, wired, optical fiber, or other connection. Data processing system 1110 then executes one or more sequences of the computer program instructions loaded into memory 1141, as a result performing process steps described herein. In this way, data processing system 1110 carries out a computer implemented process that provides for a technical effect of controlling insulin output based on inputs to a model of a biological system. For example, blocks of the flowchart illustrations or block diagrams herein, and combinations of those, can be implemented by computer program instructions. Memory 1141 can also store data used by running programs. In this example, memory 1141 (or other components in data storage system 1140) stores a base insulin delivery profile.

Computer program code can be written in any combination of one or more programming languages, e.g., Java, Smalltalk, C++, C, or an appropriate assembly language.

Program code to carry out methods described herein can execute entirely on a single data processing system 1110 or on multiple communicatively-connected data processing systems 1110. For example, code can execute wholly or partly on a user's computer and wholly or partly on a remote computer, e.g., a server. The remote computer can be connected to the user's computer through network 1150. The user's computer or the remote computer can be non-portable computers, such as conventional desktop personal computers (PCs), or can be portable computers such as tablets, cellular telephones, smartphones, or laptops.

The peripheral system 1120 can include one or more devices configured to provide digital content records or other data to the data processing system 1110. In this example, glucose monitor 1121 and glucose pump 1125 are connected to data processing system 1110 via peripheral system 1120. The monitor 1121 and the pump 1125 can also be directly connected to data processing system 1110. The peripheral system 1120 can also include digital still cameras, digital video cameras, cellular phones, biosensors such as activity sensors, heart rate monitors, pulse oximeters, or other data processors. The peripheral system 1120 can also include one or more bus bridge(s), e.g., to operatively connect devices having USB, FIREWIRE, RS-232, or other interfaces to data processing system 1110. The data processing system 1110, upon receipt of data from a device in the peripheral system 1120, can store that data in the data storage system 1140.

Data processing system 1110 is communicatively connected to interface 1131, which can include user interface system 1130 or network 1150. For example, the interface 1131 can include one or more touchscreen(s), button(s), switch(es), or network connection(s). Interface 1131 selectively receives a temporary insulin delivery profile extending over a selected time range of the time intervals and provides a first signal to data processing system 1110 indicating whether the temporary insulin delivery profile was received. This signal can be a flag set in memory in data storage system 1140 or a specific logic level or voltage on a wire or other electrical connection between interface 1131 and data processing system 1110. The signal can indicate whether or not the temporary insulin delivery profile was received using respective, different values of the signal (e.g., logic low or logic high) or by the presence or absence of the signal (e.g., a pulse is transmitted when the profile is received, so if no pulse has been transmitted, the profile has not been received). In at least one embodiment, the interface 1131 can be operated by the subject 1138, as represented graphically by the dashed line.

The user interface system 1130 can include a mouse, a keyboard, another computer (connected, e.g., via a network or a null-modem cable), a microphone and speech processor or other device(s) for receiving voice commands, a camera and image processor or other device(s) for receiving visual commands, e.g., gestures, or any device or combination of devices from which data is input to the data processing system 1110. In this regard, although the peripheral system 1120 is shown separately from the user interface system 1130, the peripheral system 1120 can be included as part of the user interface system 1130.

The user interface system 1130 also can include a display device, a processor-accessible memory, or any device or combination of devices to which data is output by the data processing system 1110. In this regard, if the user interface system 1130 includes a processor-accessible memory, such memory can be part of the data storage system 1140 even though the user interface system 1130 and the data storage system 1140 are shown separately in FIG. 8.

In various aspects, interface 1131 includes communication interface 1115 that is coupled via network link 1116 to network 1150. For example, communication interface 1115 can be an integrated services digital network (ISDN) card or a modem to provide a data communication connection to a corresponding type of telephone line. As another example, communication interface 1115 can be a network card to provide a data communication connection to a compatible local-area network (LAN), e.g., an Ethernet LAN, or wide-area network (WAN). Wireless links, e.g., WiFi or GSM, can also be used. Communication interface 1115 sends and receives electrical, electromagnetic or optical signals that carry digital data streams representing various types of information across network link 1116 to network 1150. Network link 1116 can be connected to network 1150 via a switch, gateway, hub, router, or other networking device.

Network link 1116 can provide data communication through one or more networks to other data devices. For example, network link 1116 can provide a connection through a local network to a host computer or to data equipment operated by an Internet Service Provider (ISP).

Data processing system 1110 can send messages and receive data, including program code, through network 1150, network link 1116 and communication interface 1115. For example, a server can store requested code for an application program (e.g., a JAVA applet) on a tangible non-volatile computer-readable storage medium to which it is connected. The server can retrieve the code from the medium and transmit it through the Internet, thence a local ISP, thence a local network, thence communication interface 1115. The received code can be executed by data processing system 1110 as it is received, or stored in data storage system 1140 for later execution.

The controller, e.g., data processing system 1110, is adapted to perform specific processing for each of a plurality of the discrete time intervals. Memory 1141 can store program instructions that cause data processing system 1110 to perform these processes. The data processing system 1110 receives the glucose measurement data for that time interval from the glucose monitor 1121 via the peripheral system 1120. The data processing system 1110 then determines an insulin delivery amount for that time interval using model predictive control based on a selected target glucose concentration range, the received glucose measurement data, the stored base insulin delivery profile, or, in response to the first signal and if that time interval is in the selected time range, the received temporary insulin delivery profile. This was discussed above, e.g., with reference to FIGS. 3-5 (soft and semi-soft profiles). The data processing system 1110 then provides to the insulin infusion pump 1125 a delivery control signal corresponding to the determined insulin delivery amount. The insulin infusion pump 1125 then delivers a corresponding amount of insulin, e.g., to subject 1138.

According to at least one aspect, the interface 1131 is adapted to receive the temporary insulin delivery profile by receiving change information, e.g., +1 U/h, and modifying the stored base insulin delivery profile (in data storage system 1140) in the selected time range according to the change information to provide the temporary insulin delivery profile. The interface 1131 can perform this modification by notifying data processing system 1110 about the modification to be performed, in response to which data processing system 1110 executes instructions that perform the modification.

In various embodiments, the interface 1131 is further adapted to provide an activation signal, e.g., when the subject 1138 pushes a button on the interface 1131. The data processing system 1110, in response to the activation signal, retrieves the stored base insulin delivery profile and retrieves or determines the insulin delivery amount.

In an example of using a soft profile, data processing system 1110 is programmed to determine the insulin delivery amount for a selected time interval using the selected target glucose concentration range, the received glucose measurement data, the stored base insulin delivery profile if the temporary insulin delivery profile was not received (as indicated by the signal from interface 1131 or lack thereof) or the selected time interval is outside the selected time range. Otherwise, the data processing system uses the selected target glucose concentration range, the received glucose measurement data, and the received temporary insulin delivery profile.

In an example of using a semi-soft profile, in response to the first signal and if a selected time interval is in the selected time range, the data processing system 1110 constrains the determined insulin delivery amount for the selected time interval to be at least a difference between respective values of the temporary insulin delivery profile and the stored base insulin delivery profile for the selected time interval.

In an example of using a hard profile, the data processing system 1110 is programmed to, for each of a plurality of the discrete time intervals, receive the glucose measurement data for that time interval from the glucose monitor. If that time interval is in the selected time range, the data processing system 110 retrieves a corresponding insulin delivery amount from the temporary insulin delivery profile. This is the "hard" action, as discussed above with reference to FIGS. 6 and 7. If the time interval is not in the selected time range, the data processing system 1110 determines an insulin delivery amount for that time interval using model predictive control based on a selected target glucose concentration range, the received glucose measurement data, and the base insulin delivery profile. The data processing system 1110 then provides to the insulin infusion pump 1125 a delivery control signal corresponding to the insulin delivery amount, and the pump 1125 delivers a corresponding amount of insulin. The model predictive controller can be but does not have to be operated to make predictions during the selected time range. Glucose measurements are preferably still taken and recorded in data storage system 1140 during the selected time range so that the model predictive controller will not have a burn-in period (discussed above) at the end of the selected time range.

In some embodiments, the data processing system 1110, or a safety subsystem thereof or safety component attached thereto, is programmed to predict an excursion of a glucose level of the subject 1138 from the selected target glucose range. This is done using a safety model, e.g., a hypoglycemia safety model, and at least some of the glucose measurement data for a plurality of the time intervals. The system or component then reduces the determined insulin delivery amount according to the predicted excursion.

In an example of using an extended bolus, the temporary insulin delivery profile (which can be stored in data storage system 1140) includes former and latter subranges of the selected time range. The temporary insulin delivery profile specifies higher amounts or rates of insulin delivery in the former subrange than in the latter subrange, as discussed above.

In view of the foregoing, embodiments of the invention provide improved control of temporary basals and extended boluses in glucose pumping systems. A technical effect of soft and semi-soft profiles is to provide increased control of pump operation while still maintaining the ability to correct for some deviations of blood glucose outside a desired glucose zone. A technical effect of hard profiles is to provide determined amounts of insulin for limited times without disturbing insulin delivery outside those times.

While the invention has been described in terms of particular variations and illustrative figures, those of ordinary skill in the art will recognize that the invention is not limited to the variations or figures described. For example, the closed-loop controller need not be an MPC controller but can be, with appropriate modifications by those skilled in the art, a PID controller, a PID controller with internal model control (IMC), a model-algorithmic-control (MAC) that are discussed by Percival et al., in "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. Apparatus for the delivery of insulin, the apparatus comprising:
   a) a glucose monitor adapted to measure respective glucose levels of a subject at discrete time intervals and provide respective glucose measurement data indicating each measured glucose level;
   b) an insulin infusion pump configured to deliver insulin in response to a delivery control signal;
   c) a memory configured to store a base insulin delivery profile;
   d) an interface adapted to selectively receive a temporary insulin delivery profile extending over a selected time range of the time intervals and to provide a first signal indicating whether the temporary insulin delivery profile was received; and
   e) a controller adapted to, for each of a plurality of the discrete time intervals:
      i) receive the glucose measurement data for that time interval from the glucose monitor;
      ii) determine an insulin delivery amount for that time interval using the received temporary insulin delivery profile when the time interval is in the selected time range and in response to the first signal and, when the time interval is outside the selected time range, using model predictive control based on a selected target glucose concentration range, the received glucose measurement data, and the stored base insulin delivery profile; and
      iii) provide to the insulin infusion pump a delivery control signal corresponding to the determined insulin delivery amount, whereby a corresponding amount of insulin is delivered.

2. The apparatus according to claim 1, wherein the interface is adapted to receive the temporary insulin delivery profile by receiving change information and modifying the stored base insulin delivery profile in the selected time range according to the change information to provide the temporary insulin delivery profile.

3. The apparatus according to claim 1, wherein the controller is adapted to determine the insulin delivery amount for a selected time interval using:
   a) if the temporary insulin delivery profile was not received or the selected time interval is outside the selected time range, the controller is adapted to use the selected target glucose concentration range, the received glucose measurement data, the stored base insulin delivery profile;
   b) otherwise, the controller is adapted to use the selected target glucose concentration range, the received glucose measurement data, and the received temporary insulin delivery profile.

4. The apparatus according to claim 1, wherein the controller is further adapted to, in response to the first signal and if a selected time interval is in the selected time range, constrain the determined insulin delivery amount for the selected time interval to be at least a difference between respective values of the temporary insulin delivery profile and the stored base insulin delivery profile for the selected time interval.

5. The apparatus according to claim 1, wherein the controller is further adapted to:
   a) predict an excursion of a glucose level of the subject from the selected target glucose range using a safety model and at least some of the glucose measurement data for a plurality of the time intervals; and
   b) reduce the determined insulin delivery amount according to the predicted excursion.

6. The apparatus according to claim 1, wherein the temporary insulin delivery profile defines a first subrange and a second subrange of the selected time range and wherein the temporary insulin delivery profile specifies a higher rate of insulin delivery in the first subrange and a lower rate of insulin delivery in the second subrange.

7. The apparatus according to claim 1, wherein the glucose monitor includes a plurality of glucose sensors.

8. The apparatus according to claim 1, wherein the interface is further adapted to provide an activation signal and the controller, in response to the activation signal, retrieves the stored base insulin delivery profile and retrieves or determines the insulin delivery amount.

9. Apparatus for the delivery of insulin, the apparatus comprising:
   a) a glucose monitor adapted to measure respective glucose levels of a subject at discrete time intervals and provide respective glucose measurement data indicating each measured glucose level;
   b) an insulin infusion pump configured to deliver insulin in response to a delivery control signal;
   c) a memory configured to store a base insulin delivery profile;
   d) an interface adapted to receive a temporary insulin delivery profile extending over a selected time range of the time intervals; and
   a controller adapted to, for each of a plurality of the discrete time intervals:
      i) receive the glucose measurement data for that time interval from the glucose monitor;
      ii) when that time interval is in the selected time range, retrieve a corresponding insulin delivery amount from the temporary insulin delivery profile and when the time interval is outside the selected time range, determine an insulin delivery amount for that time interval using model predictive control based on a selected target glucose concentration range, the received glucose measurement data, and the base insulin delivery profile; and
      iii) provide to the insulin infusion pump a delivery control signal corresponding to the insulin delivery amount, whereby a corresponding amount of insulin is delivered.

10. The apparatus according to claim 9, wherein the controller is further adapted to:
   a) predict an excursion of a glucose level of the subject from the selected target glucose range using a safety model and at least some of the glucose measurement data for a plurality of the time intervals; and
   b) reduce the determined insulin delivery amount according to the predicted excursion.

11. The apparatus according to claim 9, wherein the glucose monitor includes a plurality of glucose sensors.

12. The apparatus according to claim 9, wherein the interface is further adapted to provide an activation signal and the controller, in response to the received activation signal, retrieves the stored base insulin delivery profile and retrieves or determines the insulin delivery amount.

* * * * *